United States Patent [19]
Luce et al.

[11] Patent Number: 5,825,457
[45] Date of Patent: Oct. 20, 1998

[54] KERATOMETRIC ILLUMINATION SYSTEM

[75] Inventors: David A. Luce, Clarence Center; Joseph L. Zelvin, Larchmont, both of N.Y.

[73] Assignee: Leica Inc., Depew, N.Y.

[21] Appl. No.: 867,622

[22] Filed: Jun. 2, 1997

[51] Int. Cl.$^6$ .................................................. A61B 3/10
[52] U.S. Cl. ........................................................ 351/221
[58] Field of Search ................................... 351/205, 212, 351/216, 220, 221

[56] References Cited

U.S. PATENT DOCUMENTS 5,033,841  7/1991  Nishio et al. ............................ 351/212

*Primary Examiner*—Huy Mai
*Attorney, Agent, or Firm*—Bean, Kauffman & Snyder

[57] ABSTRACT

A keratometer includes illuminating optics centered along a common measurement axis in alignment with a patient's cornea and with area detection means of the keratometer. A conical reflector is positioned with its apex facing a source of collimated light, such that light incident upon the conical reflector is divided into rays expanding radially outward from the measurement axis. A frusto-conical reflector surrounds the conical reflector to receive the radially expanding rays and redirect them along the measurement axis as an annulus of light large enough to pass around the area detector to a mire ring occluder and refractor which pass a refined converging annulus of light to the cornea.

25 Claims, 5 Drawing Sheets

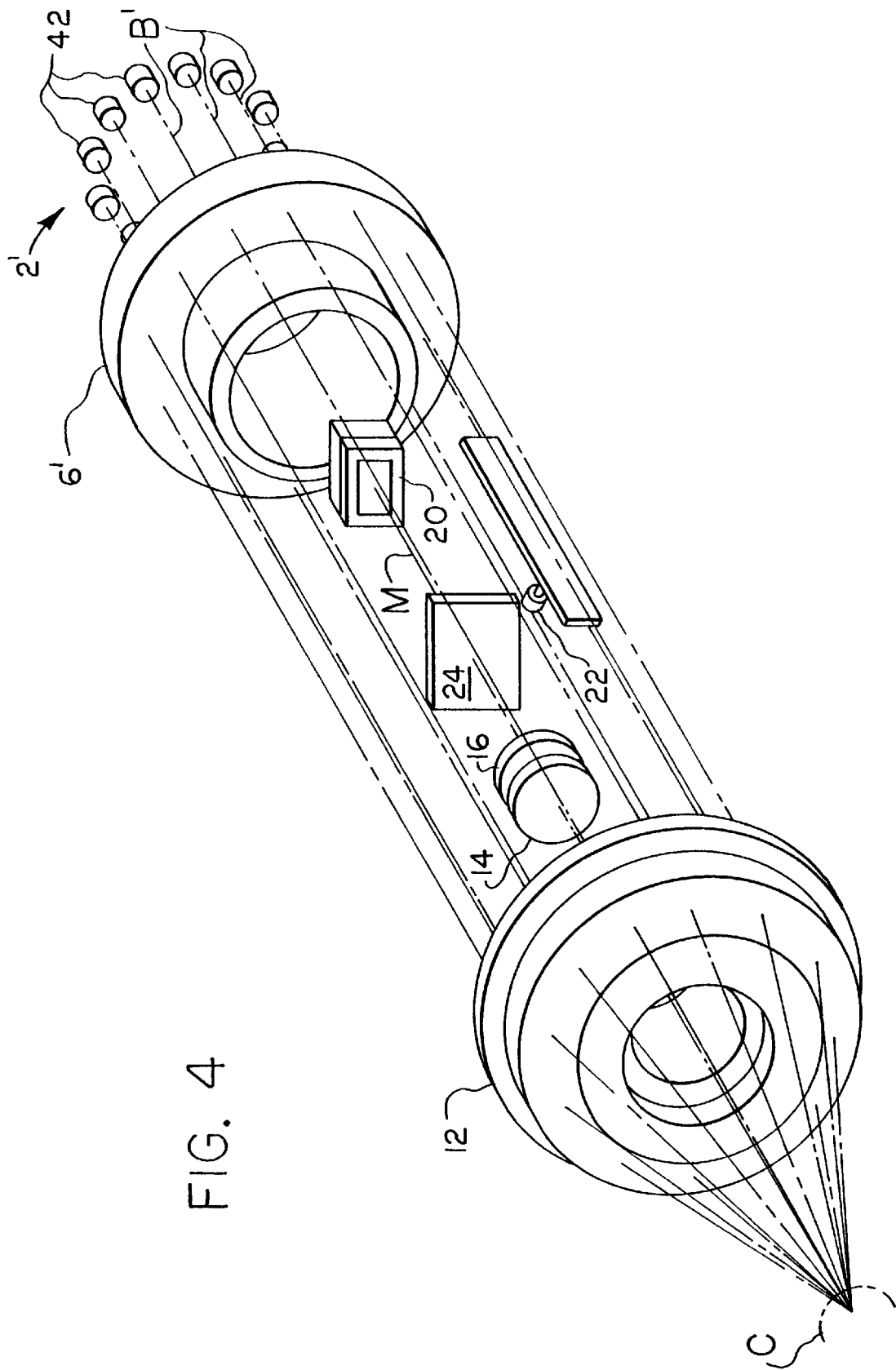

KERATOMETRIC ILLUMINATION SYSTEM

BACKGROUND OF THE INVENTION

A. Field of the Invention

This invention relates generally to a keratometric illumination system which projects an annulus of light onto a patient's eye, and more particularly to a keratometric illumination system which projects an annulus of light onto an eye with reduced energy loss and reduced light noise.

B. Description of the Prior Art

Keratometers, currently, employ a light source and a series of optical components arranged to project an annulus of light along a path for reflection by the cornea of an eye. The reflected light is received by an area detector such as a CCD, which provides a signal representative of illuminated pixels. The detector signal is processed and analyzed by software or other means to determine the configuration of the cornea.

In known keratometers, such as that disclosed in U.S. Pat. No. 5,033,841, light is projected from a light source located off of a measurement axis, through an occluder having an annular opening, and through a condenser lens to a 50/50 beam splitter which is located on the measurement axis between the cornea and the CCD. The beam splitter reflects a portion of the annular light flux through at least an objective lens to the cornea, which then reflects the light back along the measurement axis, through the objective lens, through the beam splitter, and through at least an imaging lens to the CCD. The CCD feeds signal information representing the ring image to a computer for processing the signal and calculating corneal configuration.

Keratometers of the type described above have certain inherent shortcomings. Specifically, the use of a beam splitter to introduce source light along the measurement axis drastically increases the amount of source energy needed to create the resulting image on the CCD. The output flux density (flux per unit area measured normal to the direction of propagation of the flux) of a light beam transmitted or reflected by a 50/50 beam splitter is approximately 50% of the flux density of an input source beam incident to the beam splitter. Thus, the illuminating beam of prior art constructions typically suffers a 50% reduction in flux density before reaching the eye, not including the relatively small energy losses due to absorption, scattering and reflection from other optical components in the system.

Another shortcoming is that light traveling along the measurement axis to the cornea tends to interfere with reflected light traveling back along the measurement axis from the cornea to the CCD, thus introducing a source of error in the detected image.

Finally, the use of many separate optical components introduces added manufacturing costs due to the need for accurate positioning and alignment of the components.

SUMMARY OF THE INVENTION

The present invention was developed in view of these and other shortcomings of the prior art.

Therefore, it is an object of the present invention to provide a keratometric illumination system which projects an annulus of light onto a cornea of a patient without the use of a beam splitter.

It is another object of the present invention to provide a keratometric illumination system in which reflected light from a cornea is not interfered with by light projected to the cornea.

It is a further object of the present invention to provide a keratometric illumination system wherein a plurality of the optically functional elements are contained in one optical component.

It is a further object of the present invention to provide a keratometric illumination system which contains a reduced number of optical components by incorporating both a conical reflector and a frusto-conical reflector in one optical component.

It is a further object of the present invention to provide a keratometer having an area detector located coaxially between an illuminating light source of the keratometer and a cornea to be measured.

To meet these and other objects, a keratometer formed in accordance with a preferred embodiment of the present invention incorporates a novel illumination system for illuminating a patient's cornea with an annulus of light. In a currently preferred keratometric illumination system of the present invention, the illuminating optics are centered along a common measurement axis in alignment with the cornea and with area detection means of the keratometer. A conical reflector is positioned with its apex facing a source of collimated light, such that light incident upon the conical reflector is divided into rays expanding radially outward from the measurement axis. A frusto-conical reflector surrounds the conical reflector to receive the radially expanding rays and redirect them along the measurement axis as an annulus of light large enough to pass around an area detector located on the measurement axis between the light source and the cornea. The conical and frusto-conical reflectors are preferably contained within a unitary internally reflecting prism formed of glass or plastic. A mire ring occluder is provided adjacent an entry surface of a refracting component, whereby the mire occluder and refracting component cooperate to direct a thin, well-defined converging annulus of light to the cornea. As will be appreciated, the keratometric illumination system of the present invention avoids the need for a beam splitter positioned along the measurement axis between the cornea and the area detector for the purpose of introducing an annulus of light along the measurement axis from an off-axis light source.

BRIEF DESCRIPTION OF THE DRAWINGS

The nature and mode of operation of the present invention will now be more fully described in the following detailed description taken with the accompanying drawings, in which:

FIG. 4 is an optical schematic diagram of a keratometer formed in accordance with an alternative embodiment of the present invention;

DETAILED DESCRIPTION OF THE PREFERRED EMBODIMENTS

Figure 1:
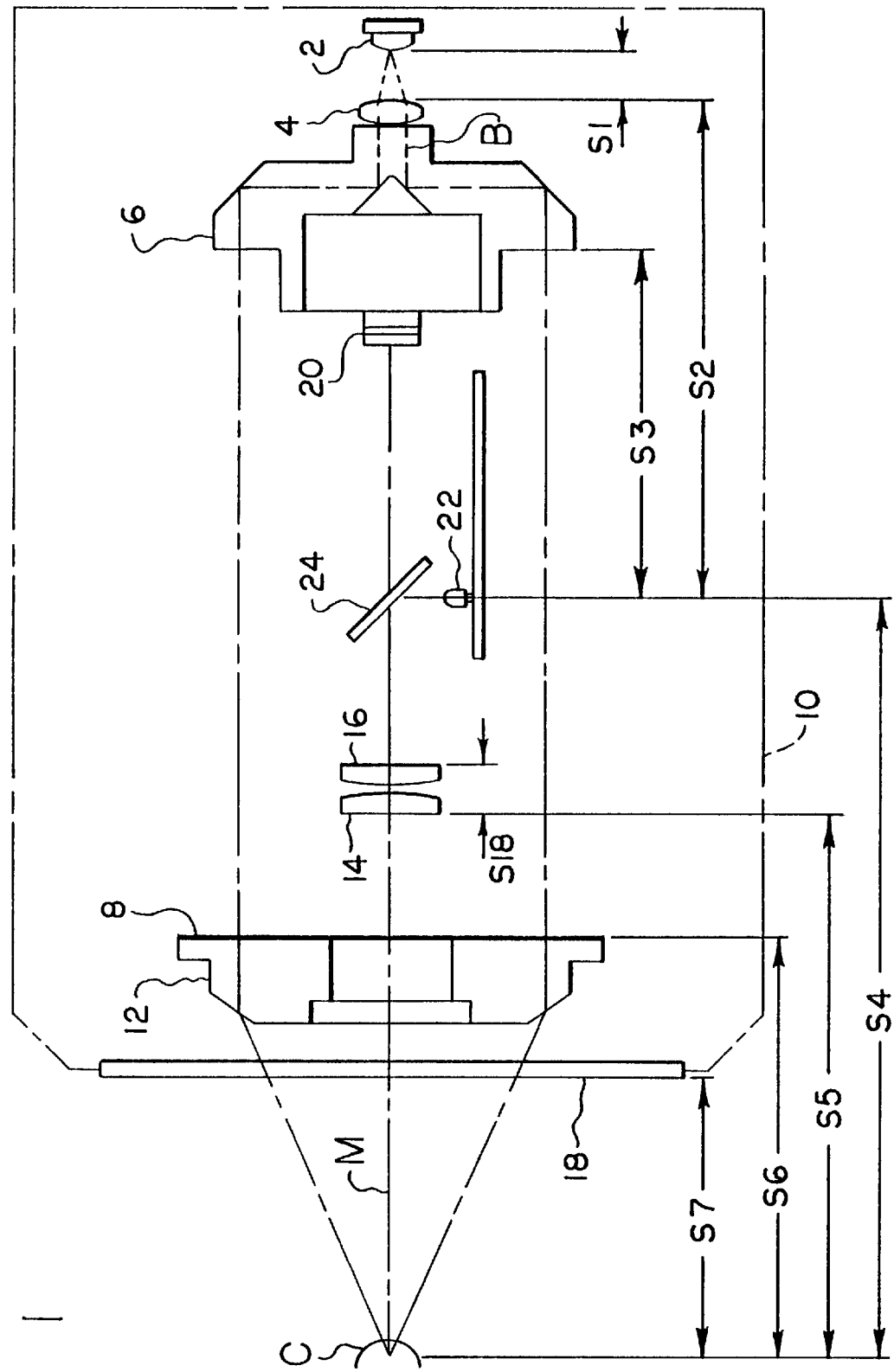
FIG. 1 is an optical schematic diagram of a keratometer formed in accordance with a preferred embodiment of the present invention.

FIG. 1 shows an optical diagram of a keratometric illumination system according to a preferred embodiment of the present invention. The depicted illumination system generally comprises a light source (2), a collimating lens (4), a prism component (6), a mire ring occluder (8), and a refractor (12) centered along a measurement axis (M) in alignment with the vertex of cornea (C). The illumination system is shown in conjunction with a pair of imaging lenses (14) and (16) for forming an image of the corneally reflected mire on an area detector (20) positioned along measurement axis (M) between the imaging lenses and prism component (6). A fixation target may be introduced along measurement axis (M) in a known manner by a target light source (22) in combination with a beam splitter (24). The above optical elements are mounted in suitable housing means represented by broken line (10) in FIG. 1. Housing (10) includes a transparent front window (18) facing the patient. The distances associated with these components in the preferred embodiment are located in FIG. 1 and listed in Table I:

TABLE I

| LABEL | DIMENSION |
|-------|-----------|
| S1 | 11.955 mm |
| S2 | 99.035 mm |
| S3 | 71.392 mm |
| S4 | 154.844 mm |
| S5 | 110.595 mm |
| S6 | 85.525 mm |
| S7 | 57.15 mm |

Alignment of cornea (C) along measurement axis (M) at a proper measurement distance is preferably carried out using an opto-electronic alignment system, not shown, as taught in commonly owned U.S. Pat. No. 4,881,807.

Light source (2) is preferably a light emitting diode (LED) which emits infrared light at approximately 880 nm for patient comfort, however other wavelengths are also contemplated. Light source (2) is located behind area detector (20) along measurement axis (M) relative to cornea (C). The diverging light rays from light source (2) are oriented into a collimated light beam (B) by collimating lens (4). Those skilled in the art will recognize that a source of collimated light, such as a laser, may be used in place of a diverging light source and collimating lens as means to produce a collimated beam of light.

Figure 3:
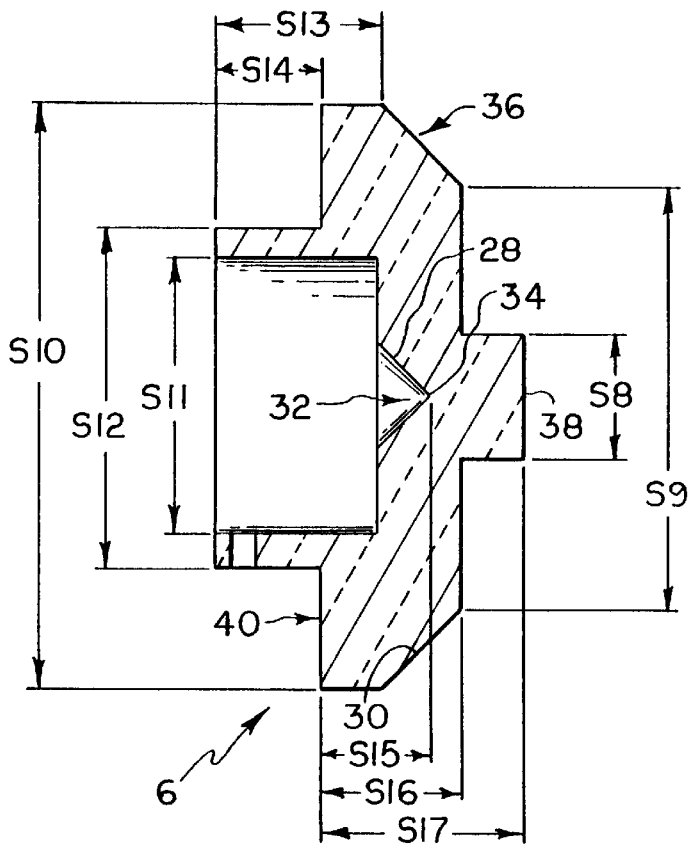
FIG. 3 is a cross-sectional view thereof taken generally along the line 3—3 in FIG. 2.
Figure 2:
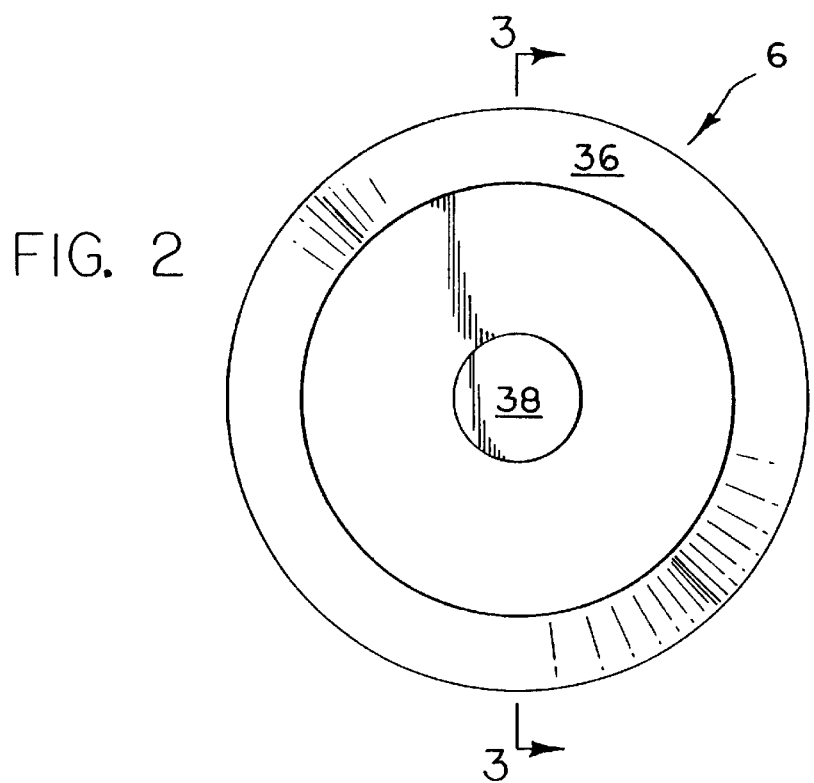
FIG. 2 is an elevational view of a prism component used in a preferred embodiment of the present invention, facing an entry surface thereof.

Prism component (6), shown in detail in FIGS. 2 and 3, is located adjacent collimating lens (4) for receiving collimated light traveling along measurement axis (M), and comprises a pair of functional optical elements, namely a conical reflector (28) and a frusto-conical reflector (30). As used herein, the term "conical" is intended to include surfaces forming a complete cone as well as surfaces forming a frusto-cone. The conical reflector (28) is axially aligned along measurement axis (M) so as to divide the collimated light beam into radially expanding rays. Frusto-conical reflector (30) surrounds conical reflector (28) to receive the radially expanding rays and redirect the radially expanding rays along measurment axis (M) as an annulus of light. In the preferred embodiment, the conical reflector (28) and frusto-conical reflector (30) are both contained in a single optical component, namely prism component (6), as internally reflecting surfaces thereof. Prism component (6) includes an internal recess (32) which defines conical reflector (28) having an apex (34) located on measurement axis (M) of the system. Prism component (6) further includes an external bevel (36) which defines frusto-conical reflector (30). In the preferred embodiment, the reflecting surface of frusto-conical reflector (30) is parallel to the reflecting surface of conical reflector (28), both surfaces being at a 45 degree angle relative to measurement axis (M). As best seen in FIG. 2, a planar entry surface (38) and a planar exit surface (40) are formed on prism component (6) parallel to the radially expanding rays. Prism component (6) is preferably made of clear acrylic optical grade material, however prism component (6) may also be made of glass. Furthermore, the surface quality of critical surfaces at recess (32), bevel (36), entry surface (38), and exit surface (40) is SP1-A2 polish grade. While conical reflector (28) and frusto-conical reflector (30) are preferably incorporated into a single optical component, they may of course be physically separate elements of the illumination system, such as mirrors, individually mounted within housing (10). Furthermore, reflectors (28) and (30) may be made up of smaller optical elements. For instance, the conical reflector may be constructed of several smaller curved reflectors. The preferred characteristics of prism component (6) are located in FIG. 2 and listed in Table II:

TABLE II

| PRISM COMPONENT (6) | |
|---|---|
| LABEL | DIMENSION |
| S9 | .625 mm |
| S10 | 2.128 mm |
| S11 | 2.915 mm |
| S12 | 1.439 mm |
| S13 | 1.750 mm |
| S14 | .795 mm |
| S15 | .500 mm |
| S16 | .591 mm |
| S17 | .689 mm |
| S18 | 1.000 mm |

Figure 6:
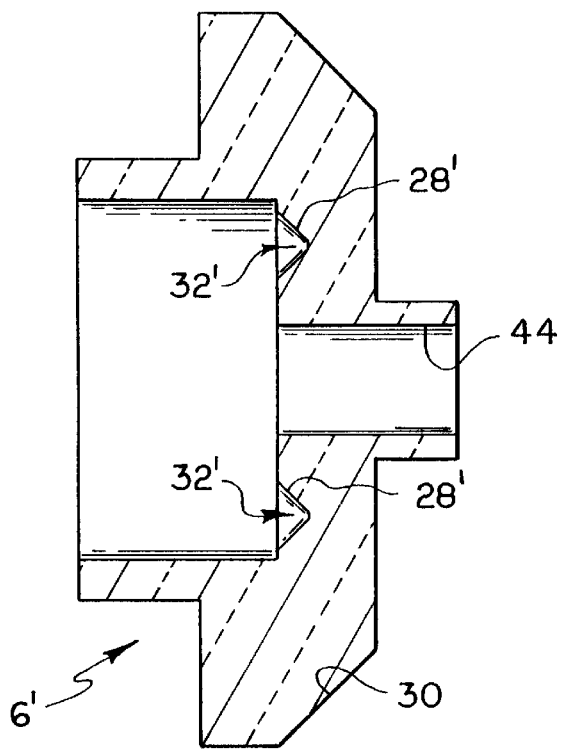
FIG. 6 is a cross-sectional view thereof taken generally along the line 6—6 in FIG. 5.
Figure 5:
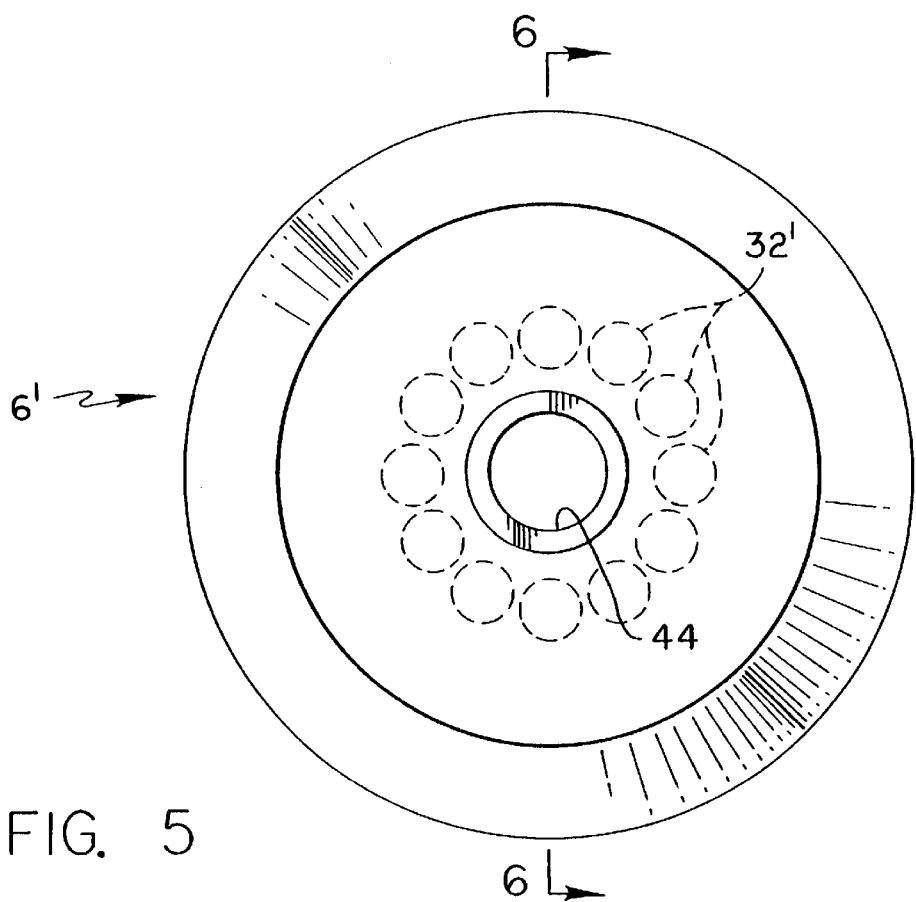
FIG. 5 is an elevational view of a prism component used in the alternative embodiment of the present invention shown in FIG. 4, facing an entry surface thereof.

In an alternative embodiment of the illumination system of the present invention illustrated schematically in FIG. 4, a light source (2') comprises a plurality of laser diodes (42) arranged in a ring pattern about measurement axis (M) to provide a plurality of collimated beams (B') angularly spaced about the measurement axis, and prism component (6'), shown also in FIGS. 5 and 6, includes a plurality of internal recesses (32') arranged in corresponding angular spacing about measurement axis (M) to define a plurality of conical reflectors (28') centered on a respective beam (B'). As in the preferred embodiment described above, light is reflected from conical reflectors (28') as radially expanding rays which are subsequently redirected by surrounding frusto-conical reflector (30) as an annulus of light along measurement axis (M). This alternative embodiment has the advantage of allowing wiring (not shown) to be passed back through an axial bore (44) in prism component (6').

Figure 8:
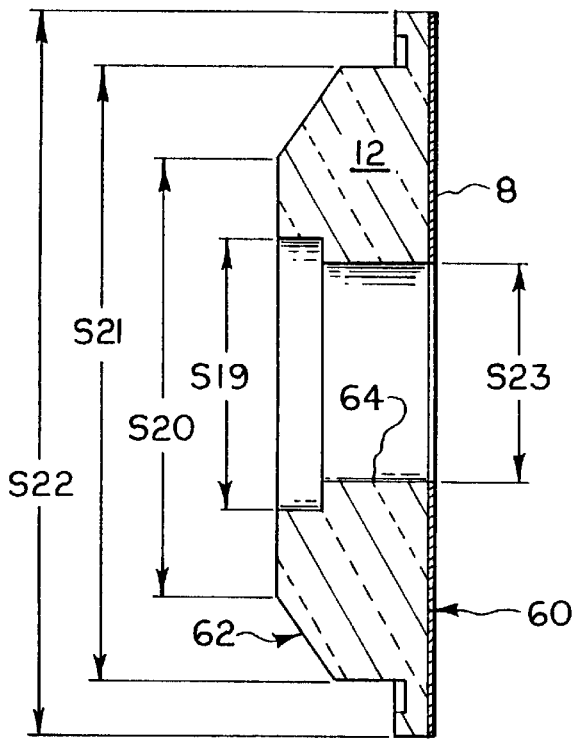
FIG. 8 is a cross-sectional view of the mire ring occluder and refractor taken generally along the line 8—8 in FIG. 7.
Figure 7:
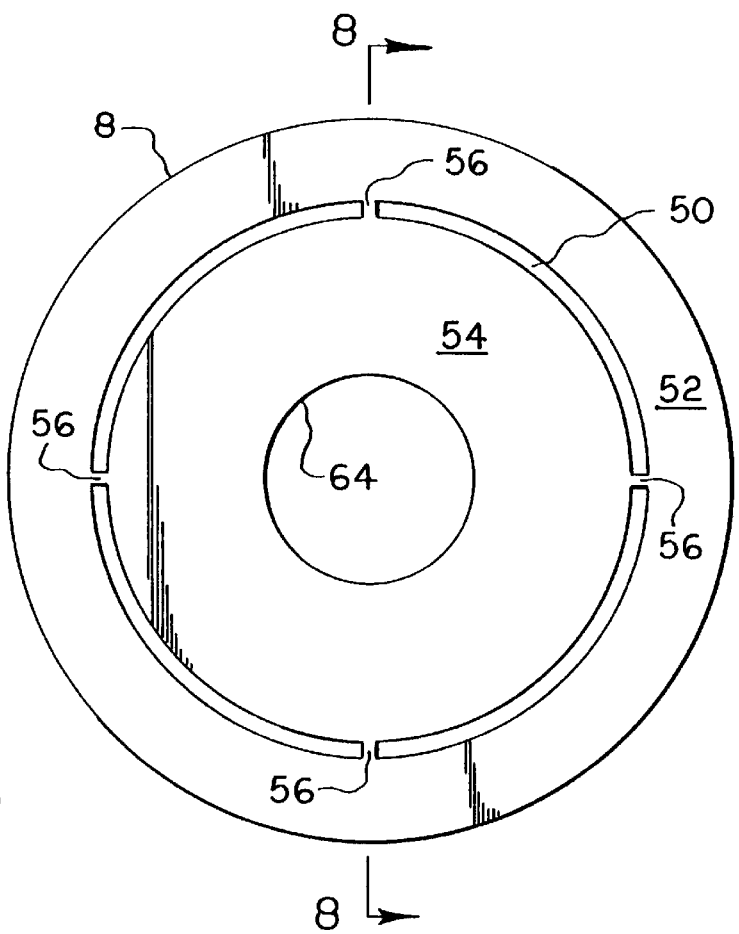
FIG. 7 is an elevational view of a mire ring occluder associated with an adjacent refractor used in a preferred embodiment of the present invention.

Referring now to FIGS. 7 and 8 in conjunction with FIG. 1, the annulus of light leaving exit surface (40) travels along measurement axis (M), passing around area detector (20), fixation target beam splitter (24), and imaging lenses (14) and (16) to reach mire ring occluder (8). Mire ring occluder (8) includes a ring-shaped opening (50) defined by an outer opaque region (52) and an inner opaque region (54), whereby the mire ring occluder blocks a portion of the annulus of light to reduce its thickness and produce a thin, well-defined annulus of the light. Mire ring occluder (8) may be formed as a coating applied to an entry surface (60) of refractor (12) orthogonal to measurement axis (M), or it may be a separately formed thin plate affixed to refractor entry surface (60) by suitable means. Where the mire ring occluder (8) is formed as a separate plate, as shown in FIG. 7, small bridges (56) connecting outer and inner opaque regions (52) and (54) are provided. In the geometry of the preferred embodiment, ring-shaped opening (50) is 64.5 mm in diameter as measured at its midpoint, with a thickness of 0.813 mm. As will be understood from subsequent description, the diameter of ring-shaped opening (50) of mire ring occluder (8) is large as compared to the diameter of the annulus of light reaching the cornea (C). Accordingly, the undesirable effects of small manufacturing imperfections in the edges bordering ring-shaped opening (50) are reduced relative to those experienced with respect to smaller diameter ring-shaped openings encountered in the prior art, resulting in a more accurately defined annulus of light incident on the cornea.

The thin annulus of light passing through mire ring occluder (8) to refractor (12) is refracted at an annular exit surface (62) thereof to provide a thin annulus of light converging about measurement axis (M) in the direction of cornea (C). The refractor (12) may be constructed of glass, plastic or any other suitable optical material; a currently preferred material is clear optical grade acrylic. The surface quality of refractor (12) is SP1-A2 polish grade at critical entry surface (60) and at critical refracting exit surface (62), which forms a 35 degree angle with vertical in FIG. 8. A stepped axial through hole (64) is provided for passage of corneally reflected light back through refractor (12) and mire ring occluder (8). The preferred dimensional characteristics of refractor (12) can be found in FIG. 8 and Table III:

TABLE III

REFRACTOR (12)

| LABEL | DIMENSION |
|---|---|
| S19 | 1.300 mm |
| S20 | 2.126 mm |
| S21 | 2.913 mm |
| S22 | 3.445 mm |
| S23 | 1.002 mm |

The cornea (C) reflects the incident annulus of light back along measurement axis (M) successively through patient window (18), through hole (64), imaging lenses (14) and (16), and fixation target beam splitter (24) to illuminate an annular area on area detector (20). The combined power of the imaging lenses is such that for an average cornea having a power of 43 diopters, the imaging lenses will produce a mirror image of the corneally reflected mire at area detector (20). Imaging lenses (14) and (16) of the preferred embodiment are spaced 10 mm from flat surface to flat surface, identified as S18 in FIG. 1. Other preferred characteristics of the imaging lenses (14) and (16) may be found in Table IV:

TABLE IV

IMAGING LENSES (14) AND (16)

| OPTICAL COMPONENT | RADIUS | THICKNESS | FOCAL LENGTH |
|---|---|---|---|
| Lens (14) | FLAT<br>75.109 mm | 4.0 mm | 100 mm |
| Lens (16) | 75.109 mm<br>FLAT | 4.0 mm | 100 mm |

Area detector (20) is preferably a CCD having a pixel array containing a plurality of rows, each row containing a plurality of light sensitive pixels. However, the area detector could also be a charge injection device (CID), vidicon, charge coupled photodiode array (CCPA) or other similar device. CCD (20) is desirably frequency sensitive to read only the frequency of light emitted by light source (2), whereby interference caused by different frequency light emitted by target light source (22) could be reduced.

The optical system of the preferred embodiment is useful for measuring corneas ranging in radius of curvature from about 5 mm to about 10 mm, a range which includes nearly 100% of the human population.

What is claimed is:

1. A keratometric illumination system comprising:
   a beam of light;
   a conical reflector centered on said beam, said conical reflector dividing said beam into radially expanding rays; and
   a frusto-conical reflector redirecting said radially expanding rays as an annulus of light.

2. The keratometric illumination system according to claim 1, wherein a solid optical component contains said conical reflector and said frusto-conical reflector.

3. The keratometric illumination system according to claim 2, wherein said component is plastic.

4. The keratometric illumination system according to claim 2, wherein said component is glass.

5. The keratometric illumination system according to claim 2, wherein said component further includes a planar exit surface parallel to said radially expanding rays.

6. The keratometric illumination system according to claim 5, wherein said component is plastic.

7. The keratometric illumination system according to claim 6, wherein said conical reflector and said frusto-conical reflector are internally reflecting surfaces of said component.

8. The keratometric illumination system according to claim 5, wherein said component is glass.

9. The keratometric illumination system according to claim 8, wherein said conical reflector and said frusto-conical reflector are internally reflecting surfaces of said component.

10. The keratometric illumination system according to claim 5, further including a diode to provide said beam as invisible light.

11. The keratometric illumination system according to claim 10, wherein said component is plastic.

12. The keratometric illumination system according to claim 10, wherein said component is glass.

13. The keratometric illumination system according to claim 5, further including an annular means for converging said annulus of light.

14. The keratometric illumination system according to claim 13, wherein said annular means refracts said annulus of light.

15. The keratometric illumination system according to claim 14, wherein said annular means includes an entrance surface parallel to said exit surface of said component, and an annular refracting surface.

16. The keratometric illumination system according to claim 15, wherein said annular means is plastic.

17. The keratometric illumination system according to claim 15, wherein said annular means is glass.

18. The keratometric illumination system according to claim 2, wherein an axis passes through the center of said annulus of light, and a plurality of beams and corresponding conical reflectors are angularly spaced about said axis.

19. A solid optical component comprising:

a central axis;

an internal recess defining a conical reflecting surface; and an external bevel defining a frusto-conical reflecting surface parallel to said conical reflecting surface;

whereby a beam of light directed at said conical reflecting surface is redirected along said axis as an annulus of light.

20. The solid optical component according to claim 19, wherein there are a plurality of said conical reflecting surfaces angularly spaced about said axis.

21. A keratometer for measuring keratometric properties of a cornea, said keratometer comprising:

a measurement axis, said cornea being aligned along said measurement axis;

an area detector arranged for receiving light reflected by said cornea;

means for providing a light flux centered on said measurement axis in the direction of said cornea, said light flux existing distally of said cornea relative to said area detector; and means for converting said light flux to an annulus of light, wherein said annulus of light passes around said area detector without interference thereby.

22. The keratometer according to claim 21, wherein said light flux is a collimated light flux.

23. The keratometer according to claim 22, wherein said means for converting said light flux to an annulus of light comprises a conical reflector centered on said measurement axis to divide said flux into radially expanding rays, and a frusto-conical reflector centered on said measurement axis and arranged to redirect said radially expanding rays as said annulus of light.

24. The keratometer according to claim 22, wherein said means for converting said light flux to an annulus of light comprises a plurality of conical reflectors angularly spaced about said measurement axis to divide said flux into radially expanding rays, and a frusto-conical reflector centered on said measurement axis and arranged to redirect said radially expanding rays as said annulus of light.

25. The keratometer according to claim 21, wherein said area detector is a charge couple device.

* * * * *